(12) United States Patent
Okada

(10) Patent No.: US 6,315,901 B1
(45) Date of Patent: Nov. 13, 2001

(54) LIQUID CHROMATOGRAPHY

(75) Inventor: Kohji Okada, Nagaokakyo (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/527,625

(22) Filed: Mar. 17, 2000

(30) Foreign Application Priority Data

Apr. 14, 1999 (JP) ................................. 11-106177

(51) Int. Cl.$^7$ ................................................. B01D 15/08
(52) U.S. Cl. .................... 210/198.2; 210/85; 210/141; 210/143; 210/656; 422/70
(58) Field of Search .................... 210/656, 85, 141, 210/143, 198.2; 422/70; 702/23, 30, 32; 73/61.52; 436/161

(56) References Cited

U.S. PATENT DOCUMENTS

| | | | |
|---|---|---|---|
| 5,350,520 | * 9/1994 | Kikumoto | 210/198.2 |
| 5,358,639 | * 10/1994 | Yasuda | 210/198.2 |
| 5,407,569 | * 4/1995 | Greenley | 210/198.2 |
| 5,443,734 | * 8/1995 | Fetner | 210/656 |
| 5,457,626 | * 10/1995 | Wolze | 210/198.2 |
| 5,531,959 | * 7/1996 | Johnson | 210/198.2 |
| 5,670,379 | * 9/1997 | Ito | 210/198.2 |
| 5,730,867 | * 3/1998 | Drew | 210/198.2 |
| 5,738,783 | * 4/1998 | Shirota | 210/198.2 |
| 5,755,559 | * 5/1998 | Allington | 210/198.2 |
| 5,827,946 | * 10/1998 | Klee | 210/198.2 |
| 5,830,353 | * 11/1998 | Henderson | 210/198.2 |
| 5,938,931 | * 8/1999 | Ono | 210/198.2 |
| 6,036,856 | * 3/2000 | Ono | 210/198.2 |
| 6,221,251 | * 4/2001 | Ono | 210/198.2 |

* cited by examiner

Primary Examiner—Ernest G. Therkorn
(74) Attorney, Agent, or Firm—Kanesaka & Takeuchi

(57) ABSTRACT

A liquid chromatography includes a mobile phase quantity integrator for calculating a quantity of a mobile phase used in the liquid chromatography and sent by a fluid pump after a waste fluid in a drainage reservoir has been emptied, a rinsing fluid quantity integrator for integrating a quantity of a rinsing fluid used in a sample introducing section after the waste fluid in the drainage reservoir has been emptied, and a waste fluid quantity calculation unit for calculating a quantity of the waste fluid stored in the drainage reservoir based on the quantity of the mobile phase calculated by the mobile phase quantity integrator and the quantity of the rinsing fluid calculated by the rinsing fluid quantity integrator. A display unit displays the quantity of the waste fluid calculated by the waste fluid quantity calculation unit.

6 Claims, 7 Drawing Sheets

LIQUID CHROMATOGRAPHY

BACKGROUND OF THE INVENTION AND RELATED ART STATEMENT

The present invention relates to a liquid chromatography which isolates and analyzes various chemical substances by moving the chemical substances with a mobile phase using a column.

A traditional high-speed liquid chromatography sometimes has a function of being able to check a remaining quantity of a mobile phase stored in the instrument on its monitor in order to prevent the interruption of analysis due to insufficient mobile phase during the course of continuous analysis. An operator manually calculates a quantity of the mobile phase required for continuous analysis and decides whether any mobile phase should be added by comparing the required quantity of the mobile phase with the remaining quantity of the mobile phase displayed on the monitor.

The continuous analysis requires a sufficient amount of rinsing fluid or liquid to be used in an auto-sampling unit. If the rinsing fluid supplied to the instrument does not suffice, more rinsing fluid should be added. To check the remaining quantity of the rinsing fluid installed in the instrument, an operator has to look at the rinsing fluid reservoir. This task is troublesome for the operator.

Also, it is necessary to check how much of the drained mobile phase and drained rinsing fluid is filled in the drainage reservoir. Since the operator has to actually look at the drainage reservoir to check the quantity of the waste fluid, it is inconvenient. If checking the quantity of the accumulating waste fluid is forgotten, the drainage reservoir may sometimes overflow.

Further, an operator has to manually calculate how much mobile phase is required for the continuous analysis at the beginning of the continuous analysis. Still further, the operator has to decide whether the remaining quantity of the mobile phase is sufficient for the continuous analysis by comparing the required quantity of the mobile phase with the remaining quantity of the mobile phase. These tasks are troublesome for the operator.

The purpose of this invention is to provide a liquid chromatography for reducing operator's tasks regarding the mobile phase, rinsing fluid, and waste fluid.

SUMMARY OF THE INVENTION

A liquid chromatography of the invention is basically formed of a column for separating a sample, a mobile phase reservoir for storing a mobile phase, a fluid pump connected to the mobile phase reservoir for sending the mobile phase to the column, a sample introducing section situated between the fluid pump and the column for providing the sample into the mobile phase, a rinsing fluid reservoir connected to the sample introducing section and storing a rinsing fluid or liquid for cleaning the sample introducing section by the rinsing fluid, and a drainage reservoir connected to the column and the sample introducing section for storing a used mobile phase and used rinsing fluid as a waste fluid or liquid.

The liquid chromatography of the invention further includes a mobile phase quantity integrator for calculating a quantity of the mobile phase sent by the fluid pump after the waste fluid in the drainage reservoir has been discarded and the drainage reservoir has been emptied, a rinsing fluid quantity integrator for integrating a quantity of the rinsing fluid used in the sample introducing section after the waste fluid in the drainage reservoir has been discarded and the drainage reservoir has been emptied, a waste fluid quantity calculation unit electrically connected to the mobile phase quantity integrator and the rinsing fluid quantity integrator for calculating a quantity of the waste fluid stored in the drainage reservoir based on the quantity of the mobile phase calculated by the mobile phase quantity integrator and the quantity of the rinsing fluid calculated by the rinsing fluid quantity integrator, and a display unit electrically connected to the waste fluid calculation unit for displaying the quantity of the waste fluid calculated by the waste fluid quantity calculation unit.

DETAILED DESCRIPTION OF PREFERRED EMBODIMENTS

Figure 1:
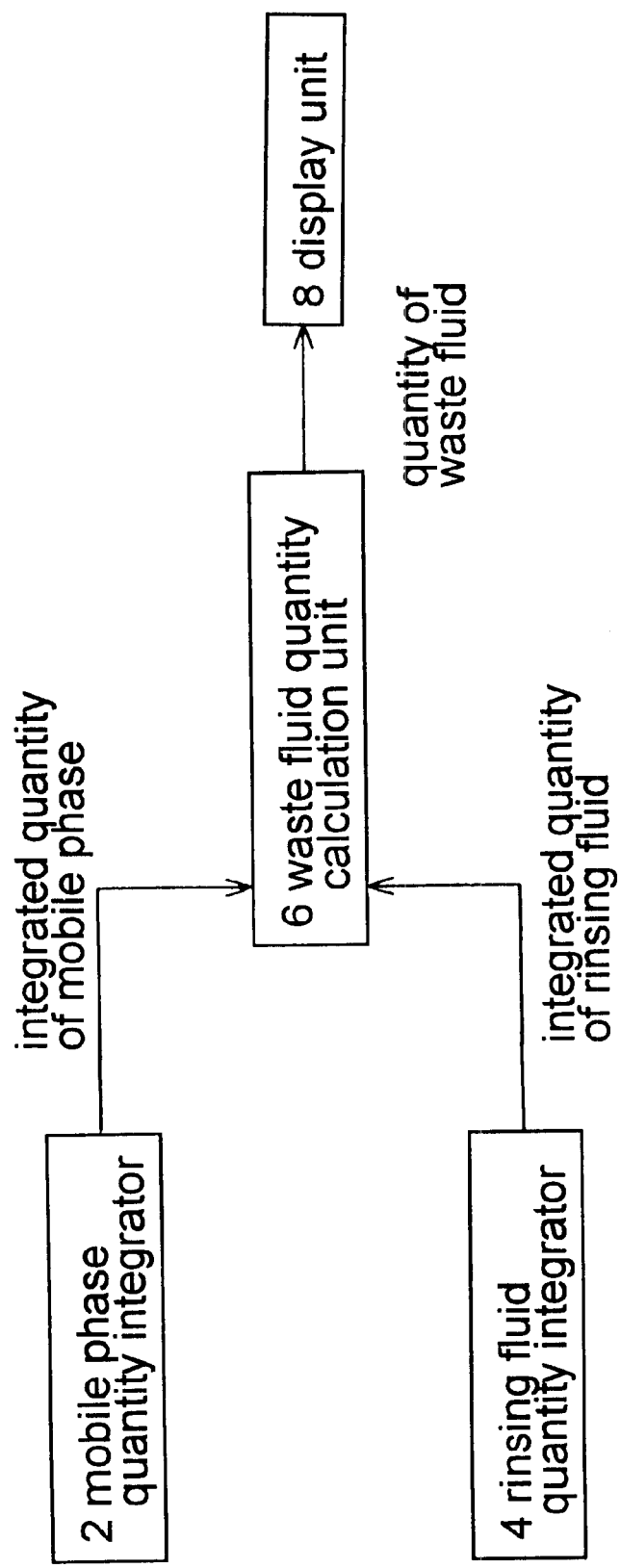
FIG. 1 is a block diagram of essential parts of the first embodiment of the invention.

FIG. 1 is a block diagram of the essential parts of the first aspect of the invention. Block 2 is a mobile phase quantity integrator calculator for integrating or calculating the quantity of the mobile phase sent by a fluid pump. Block 4 is a rinsing fluid quantity integrator for integrating the quantity of a rinsing fluid or liquid used in a sample injector or introducing section. Block 6 is a waste fluid quantity calculation unit for calculating the used mobile phase and rinsing fluid drained into a drainage reservoir based on the used quantity of the mobile phase integrated by the mobile phase quantity integrator 2 and the used quantity of the rinsing fluid integrated by rinsing fluid quantity integrator 4. A display 8 is connected to the waste fluid quantity calculation unit 6 and displays the calculated quantity of the waste fluid.

That is, in the first aspect of the invention, a liquid chromatography system comprises a column for separating the component parts of a sample, a mobile phase reservoir for storing the mobile phase, a fluid pump for sending the mobile phase to the column, a sample injector or introducing section for introducing the sample into the mobile phase in a path between the fluid pump and the column, a rinsing fluid reservoir for storing the rinsing fluid or liquid for cleaning the sample injector, a column oven for keeping the column at a constant temperature, a detector for detecting the isolated components separated by the column, and a drainage reservoir for storing the used mobile phase and rinsing fluid as waste fluid. The liquid chromatography system further includes the mobile phase quantity integrator 2 for integrating or calculating a quantity of the mobile phase sent by the fluid pump after the waste fluid in the drainage reservoir has been discarded and the drainage reservoir has been emptied, the rinsing fluid quantity integrator 4 for integrating or calculating a quantity of the rinsing fluid used in the sample injector after the waste fluid in the drainage reservoir has been discarded and the drainage reservoir has been emptied, the waste fluid quantity calculation unit 6 for calculating the quantity of the waste fluid stored in the drainage reservoir based on the quantity of the mobile phase integrated by the mobile phase quantity integrator 2 and the quantity of the rinsing fluid integrated by the rinsing fluid quantity integrator 4, and a display unit 8 for displaying the quantity of the waste fluid calculated by the waste fluid quantity calculation unit 6.

The mobile phase quantity integrator 2 integrates and memorizes the quantity of the mobile phase sent by the fluid pump. The rinsing fluid quantity integrator 4 integrates and memorizes the quantity of the rinsing fluid used in the sample injector. The mobile phase quantity integrator 2 and the rinsing fluid quantity integrator 4 reset the memorized values of the integrated quantity of the mobile phase and rinsing fluid, respectively, when the waste fluid in the drainage reservoir has been discarded and the drainage reservoir has been emptied. And, from this point, the mobile phase quantity integrator 2 integrates the quantity of the mobile phase sent by the fluid pump, and the rinsing fluid quantity integrator 4 integrates the quantity of the rinsing fluid used in the sample injector.

The mobile phase quantity integrator 2 and rinsing fluid quantity integrator 4 send the values of the integrated quantities of the mobile phase and rinsing fluid, respectively, to the waste fluid quantity calculation unit 6. The waste fluid quantity calculation unit 6 calculates the quantity of the waste fluid by adding the values of integrated quantities of the mobile phase and rinsing fluid, and send the value of the quantity of the waste fluid to the display unit 8. The display unit 8 displays the quantity of the waste fluid.

The operator can easily check the quantity of the waste fluid by looking at the display unit 8.

Figure 2:
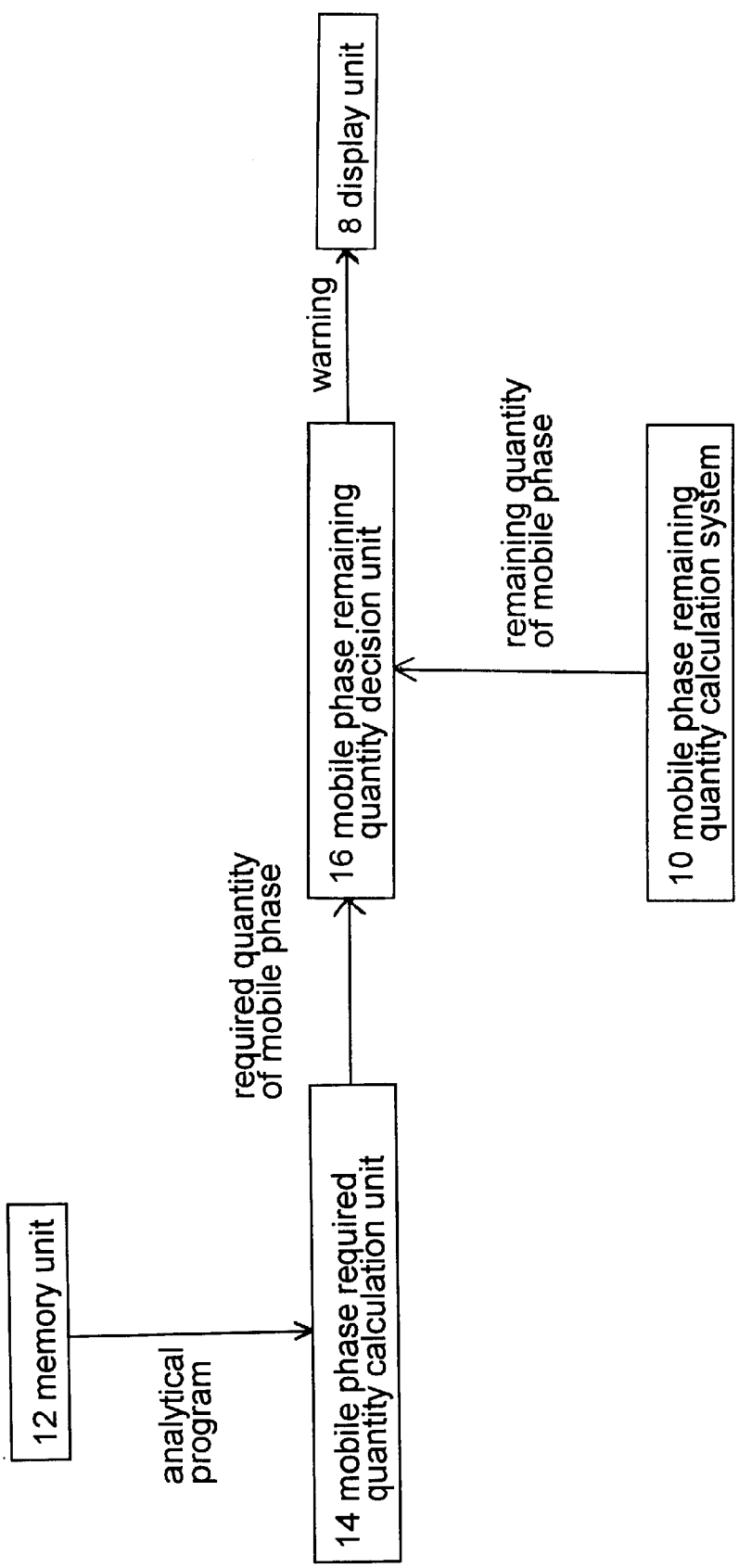
FIG. 2 is a block diagram of essential parts of the second embodiment of the invention.

FIG. 2 is a block diagram of the essential parts of the second aspect of the invention. A mobile phase remaining quantity calculation system 10 is equipped for obtaining the remaining quantity of the mobile phase stored in the mobile phase reservoir. Block 12 is a memory unit for storing an analytical program. The memory unit 12 is connected to a mobile phase required quantity calculation unit 14 for calculating the quantity of the mobile phase to be used in a continuous analysis. A mobile phase remaining quantity decision unit 16 which decides whether or not the mobile phase is sufficient for the continuous analysis is connected to the mobile phase required quantity calculation unit 14. Connected to the mobile phase remaining quantity decision unit 16, are the mobile phase remaining quantity calculation system 10 and the display unit 8 which displays a waning when the mobile phase is insufficient.

That is, in the second aspect of the invention, a liquid chromatography comprises a column for separating a sample into its components, a mobile phase reservoir for storing a mobile phase, a fluid pump for sending the mobile phase to the column, a sample injector or introducing section for introducing the sample into the mobile phase in a path between the fluid pump and the column, a column oven to keep the column at a constant temperature, a detector for detecting isolated components separated by the column, and a memory unit 12 for storing an analytical program. The liquid chromatography further includes the mobile phase remaining quantity calculation system 10 for obtaining the remaining quantity of the mobile phase stored in the mobile phase reservoir, the mobile phase required quantity calculation unit 14 for calculating the quantity of the mobile phase to be used in the continuous analysis based on the flow rate of the fluid pump and analytical program stored in the memory unit, the mobile phase remaining quantity decision unit 16 which decides whether or not the mobile phase is sufficient for the continuous analysis based on the remaining quantity of the mobile phase calculated by the mobile phase remaining quantity calculation system 10 and the required quantity of the mobile phase calculated by the mobile phase required quantity calculation unit 14, starts continuous analysis if it is sufficient, and provides a warning if it is insufficient, and the display unit 8 which displays a warning given by the mobile phase remaining quantity decision unit.

The mobile phase remaining quantity calculation system 10 obtains the value of the remaining quantity of the mobile phase stored in the mobile phase reservoir and sends the value of the remaining quantity of the mobile phase to the mobile phase remaining quantity decision unit 16 before the start of the continuous analysis. The mobile phase required quantity calculation unit 14 calculates the quantity of the mobile phase required for the continuous analysis based on the flow rate of the fluid pump and the analytical program of the continuous analysis stored in the memory unit 12, and sends the value of the required quantity of the mobile phase to the mobile phase remaining quantity decision unit 16. The mobile phase remaining quantity decision unit 16 compares the values of the remaining quantity of the mobile phase and the required quantity of the mobile phase, and decides whether there is a sufficient mobile phase for the continuous analysis. And it starts the continuous analysis if the mobile phase is sufficient for the continuous analysis, and gives a warning if it is insufficient. The display unit 8 displays the warning if the mobile phase is insufficient.

As described above, the calculation of the required quantity of the mobile phase in the continuous analysis and the decision whether or not the remaining quantity of the mobile phase is sufficient for the continuous analysis can be carried out automatically.

Figure 3:
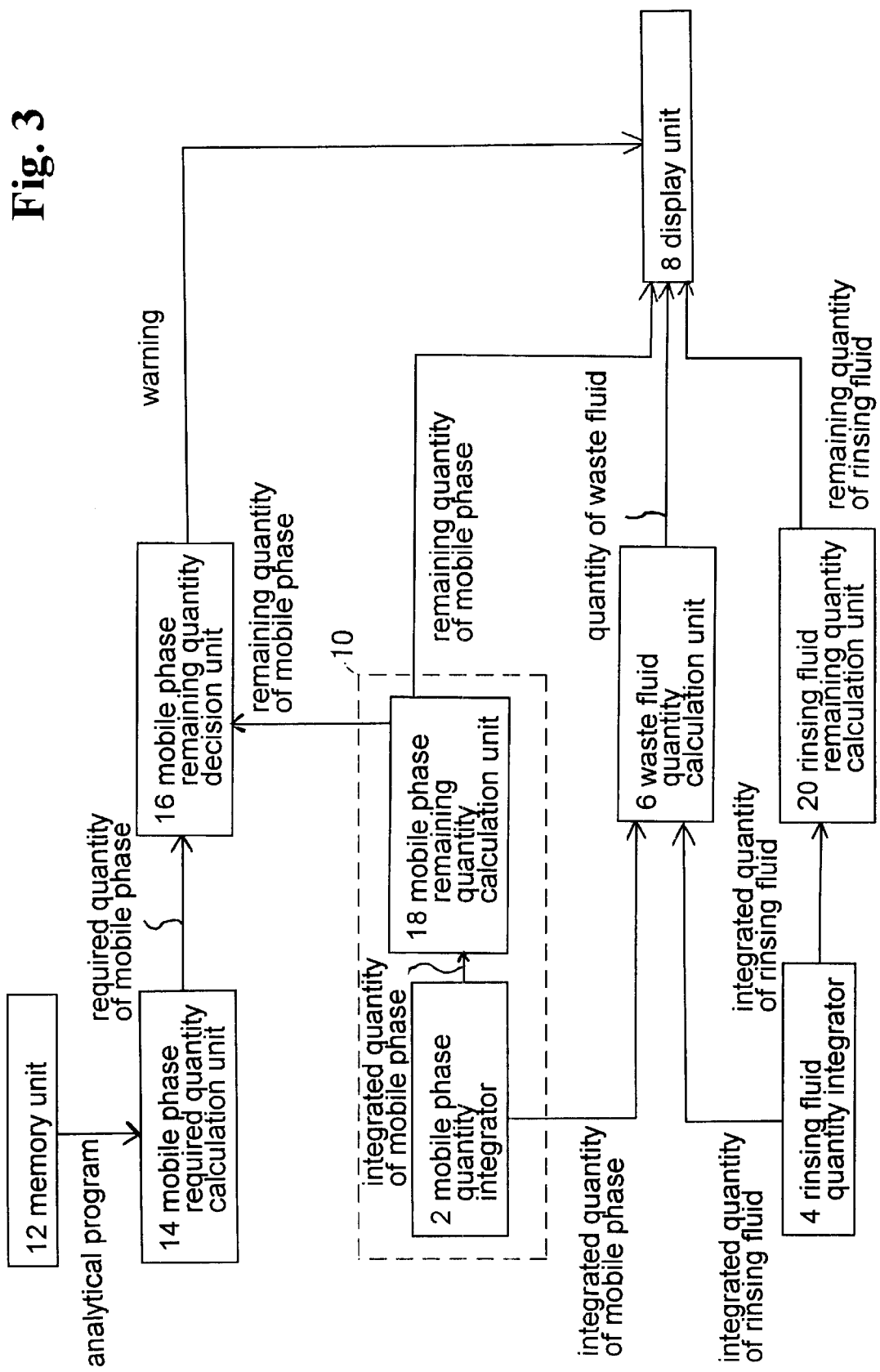
FIG. 3 is a block diagram of essential parts in a different embodiment of the first embodiment.

FIG. 3 is a block diagram of the essential parts in a different embodiment of the first aspect of the invention. This embodiment contains the functions of both the first and second aspects of the invention. Descriptions of the parts identical to those explained in FIG. 1 and FIG. 2 will be omitted here.

The mobile phase quantity integrator 2 memorizes the value of the integrated quantity of the mobile phase after the waste fluid in the drainage reservoir has been discarded and the drainage reservoir has been emptied, and also the value of the integrated quantity of the mobile phase after the mobile phase has been added to the mobile phase reservoir. This mobile phase quantity integrator 2 is connected to a mobile phase remaining quantity calculation unit 18 for calculating the remaining quantity of the mobile phase stored in the mobile phase reservoir. The mobile phase remaining quantity calculation unit 18 is connected to the display unit 8 and mobile phase remaining quantity decision unit 16. The mobile phase remaining quantity calculation system 10 of the second aspect is formed of the mobile phase quantity integrator 2 and mobile phase remaining quantity calculation unit 18.

The rinsing fluid quantity integrator 4 memorizes the value of the integrated quantity of the rinsing fluid after the waste fluid in the drainage reservoir has been discarded and the drainage reservoir has been emptied, and also the value of the integrated quantity of the rinsing fluid after the rinsing fluid has been added to the rinsing fluid reservoir. The rinsing fluid quantity integrator 4 is connected to a rinsing fluid remaining quantity calculation unit 20 for calculating the remaining quantity of rinsing fluid stored in the rinsing fluid reservoir. This rinsing fluid remaining quantity calculation unit 20 is connected to the display unit 8.

That is, this embodiment enables the following functions in addition to the functions shown in FIG. 1. The mobile phase quantity integrator 2 can integrate the quantity of the mobile phase sent by the fluid pump after the mobile phase has been added to the mobile phase reservoir; the rinsing fluid quantity integrator 4 can integrate the quantity of the rinsing fluid used in the sample injector after the rinsing fluid has been added to the rinsing fluid reservoir; the mobile phase remaining quantity calculation unit 18 calculates the remaining quantity of the mobile phase stored in the mobile phase reservoir based on the quantity of the mobile phase sent by the fluid pump integrated by the mobile phase quantity integrator 2 after the mobile phase has been added to the mobile phase reservoir, and the stored quantity of the mobile phase in the mobile phase reservoir just after the mobile phase has been added; the rinsing fluid remaining quantity calculation unit 20 calculates the remaining quantity of the rinsing fluid based on the quantity of the rinsing fluid used in the sample injector integrated by the rinsing fluid quantity integrator after the rinsing fluid has been added to the rinsing fluid reservoir, and the stored quantity of the rinsing fluid just after the rinsing fluid has been added; the memory unit 12 stores analytical programs; the mobile phase required quantity calculation unit 14 calculates the quantity of the mobile phase to be used in the continuous analysis based on the flow rate of the fluid pump and the analytical program stored in the memory unit 12; the mobile phase remaining quantity decision unit 16 decides whether or not the mobile phase is sufficient for the continuous analysis based on the remaining quantity of the mobile phase calculated by the mobile phase remaining quantity calculation unit 18 and the required quantity of the mobile phase calculated by mobile phase required quantity calculation unit 14, starts the continuous analysis if the mobile phase is sufficient, and gives a warning if the mobile phase is insufficient; and the display unit 8 can display the remaining quantity of the mobile phase calculated by the mobile phase remaining quantity calculation unit 18, the remaining quantity of the rinsing fluid calculated by the rinsing fluid remaining quantity calculation unit 20, and a warning given by the mobile phase remaining quantity decision unit 16.

The mobile phase quantity integrator 2 memorizes the values of the integrated quantity of the mobile phase after the waste fluid stored in the drainage reservoir has been discarded and the drainage reservoir has been emptied, and the integrated quantity of the mobile phase after the mobile phase has been added to the mobile phase reservoir, separately. The mobile phase remaining quantity calculation unit 18 calculates the remaining quantity of the mobile phase stored in the mobile phase reservoir based on the integrated quantity of the mobile phase which is integrated by the mobile phase quantity integrator 2 after the mobile phase has been added to the mobile phase reservoir, and the stored quantity of the mobile phase in the mobile phase reservoir just after the mobile phase has been added.

This mobile phase remaining quantity calculation unit 18 also sends the value of the remaining quantity of the mobile phase calculated by itself to the mobile phase remaining quantity decision unit 16. The mobile phase remaining quantity decision unit 16 compares the values of the remaining quantity of the mobile phase and the required quantity of the mobile phase sent by the mobile phase required quantity calculation unit 14, and decides whether or not there is a sufficient mobile phase for the continuous analysis.

The rinsing fluid quantity integrator 4 memorizes the value of the integrated quantity of the rinsing fluid after the waste fluid in the drainage reservoir has been discarded and the drainage reservoir has been emptied, and also the value of the integrated quantity of the rinsing fluid after the rinsing fluid has been added to the rinsing fluid reservoir, separately. The rinsing fluid remaining quantity calculation unit 20 calculates the remaining quantity of the rinsing fluid stored in the rinsing fluid reservoir based on the integrated quantity of the rinsing fluid integrated by the rinsing fluid quantity integrator 4 after the rinsing fluid has been added to the rinsing fluid reservoir and the stored quantity of the rinsing fluid in the rinsing fluid reservoir just after the rinsing fluid has been added.

The display unit 8 displays the quantities of the waste fluid calculated by the waste fluid quantity calculation unit 6, the remaining quantity of the mobile phase calculated by the mobile phase remaining quantity calculation unit 18, the remaining quantity of the rinsing fluid calculated by the rinsing fluid remaining quantity calculation unit 20, and a warning given by the mobile phase remaining quantity decision unit 16.

In this embodiment, an operator can easily check the quantity of the waste fluid, the remaining quantity of the mobile phase, and the remaining quantity of the rinsing fluid by looking at the display unit 8. Moreover, since the calculation of the required quantity of the mobile phase in the continuous analysis and the decision whether or not the remaining quantity of the mobile phase is sufficient for the continuous analysis are carried out automatically, the operator's load can be reduced.

Figure 4:
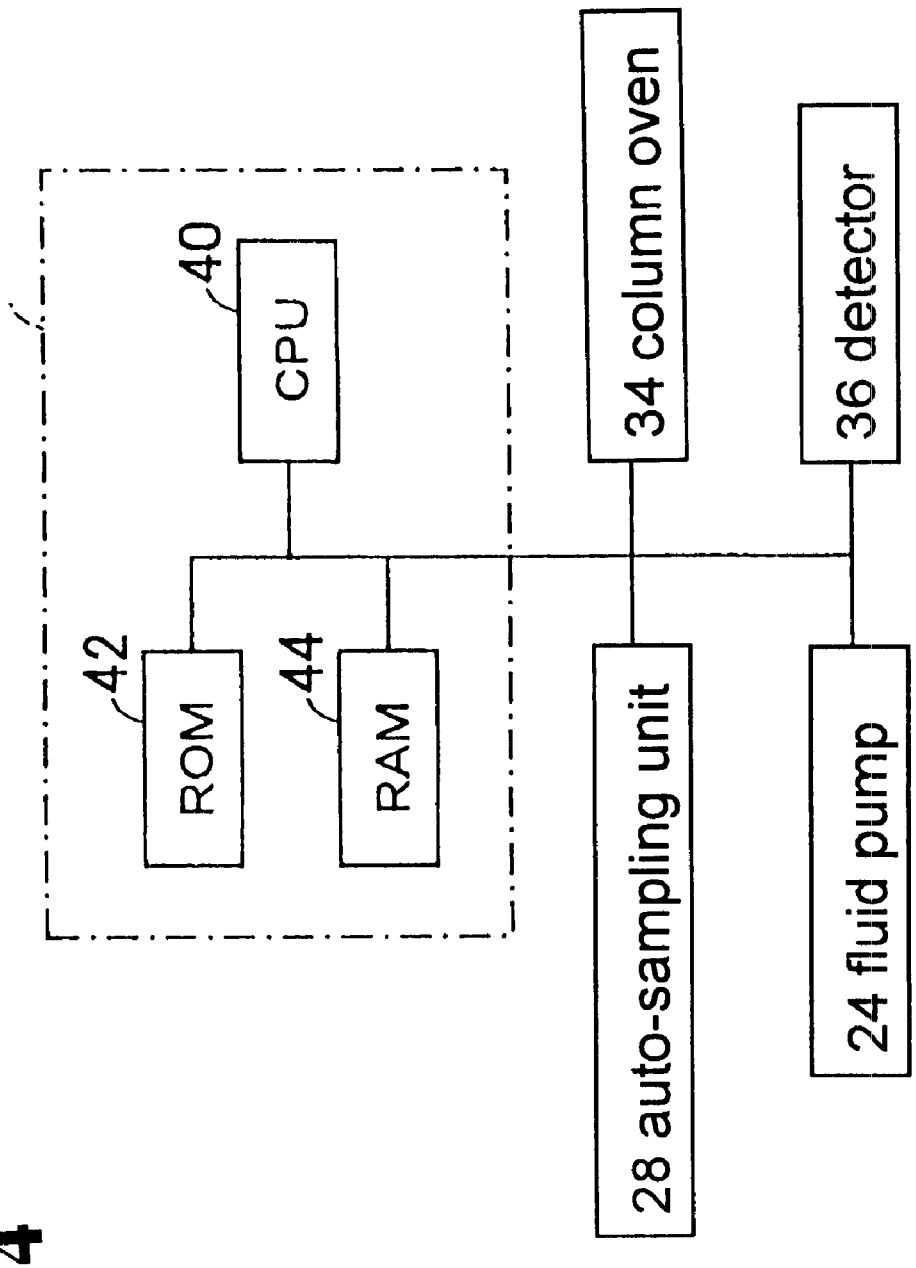
FIG. 4 is a block diagram of the outline of one example.
Figure 5:
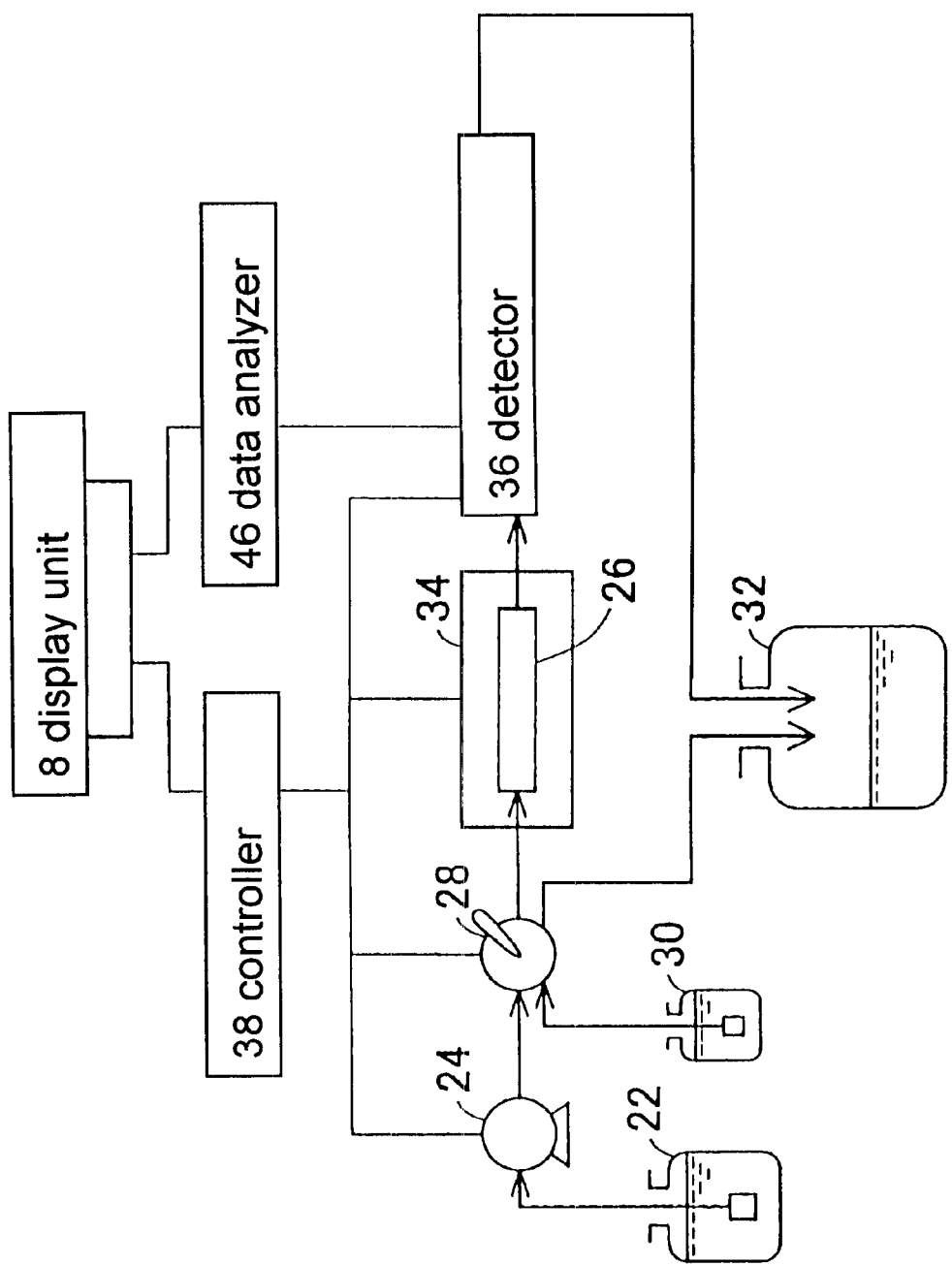
FIG. 5 is a schematic outline of the same example as shown in FIG. 4.

FIG. 4 is a block diagram of the outline of another example. FIG. 5 is a schematic outline of the example. This example realizes the functions shown in FIG. 3.

A mobile phase is sent by a fluid pump 24 from a mobile phase reservoir 22 to a column 26. An auto-sampling unit 28 installed in a path between the fluid pump 24 and the column 26 corresponds to the sample injector or introducing section, which provides a sample into the mobile phase. This auto-sampling unit 28 is connected to a path from a rinsing fluid reservoir 30. A drainage path of the rinsing fluid from the auto-sampling unit 28 is connected to a drainage reservoir 32. A column 26 is placed in a column oven 34 and maintained at a constant temperature. The downstream exit of the column 26 is connected to a detector 36 which detects the isolated sample components separated by the column, and is connected to drainage reservoir 32.

Each of the fluid pump 24, auto-sampling unit 28, column oven 34, and detector 36 is connected to a controller 38 and each operation is controlled by the controller 38. This controller 38 is formed of CPU 40, ROM 42 which stores the operation program, and RAM 44 which temporarily stores an analytical program and the values of the integrated quantities of the mobile phase, rinsing fluid, etc. Detector signals from a detector 36 are sent to a data analyzer 46 where the identification and quantification of the detected peaks are carried out. The controller 38 and data analyzer 46 are connected to the display unit 8.

The mobile phase quantity integrator 2, rinsing fluid quantity integrator 4, waste fluid quantity calculation unit 6, mobile phase required quantity calculation unit 14, mobile phase remaining quantity decision unit 16, mobile phase remaining quantity calculation unit 18, and rinsing fluid remaining quantity calculation unit 20 of this invention are formed by the CPU 40, ROM 42 and RAM 44, and the memory unit 12 of this invention is formed by the RAM 44.

The operation for a sample analysis in this example will be explained below. The column 26 is set in the column oven 34 and connected to the paths. The mobile phase is sent to the column 26 by the fluid pump 24 driven by the controller 38. The column oven 34 is turned on and the temperature of the column 26 is kept constant. After the detector signal from the detector 36 is stabilized, a sample is injected into the path by the auto-sampling unit 28 driven by the controller 38. The injected sample is separated by the column 26 and isolated components are detected by the detector 36. The detector signal from the detector 36 is sent to the data analyzer 46, where the identification and quantification of the isolated components are carried out.

The internal paths of the auto-sampling unit 28 are cleaned at every sample injection with the rinsing fluid drawn from the rinsing fluid reservoir 30 in order to prevent contamination between the samples.

The used mobile phase drained from the detector 36 and the used rinsing fluid drained from the auto-sampling unit 28 are stored in the drainage reservoir 32.

Figure 6:
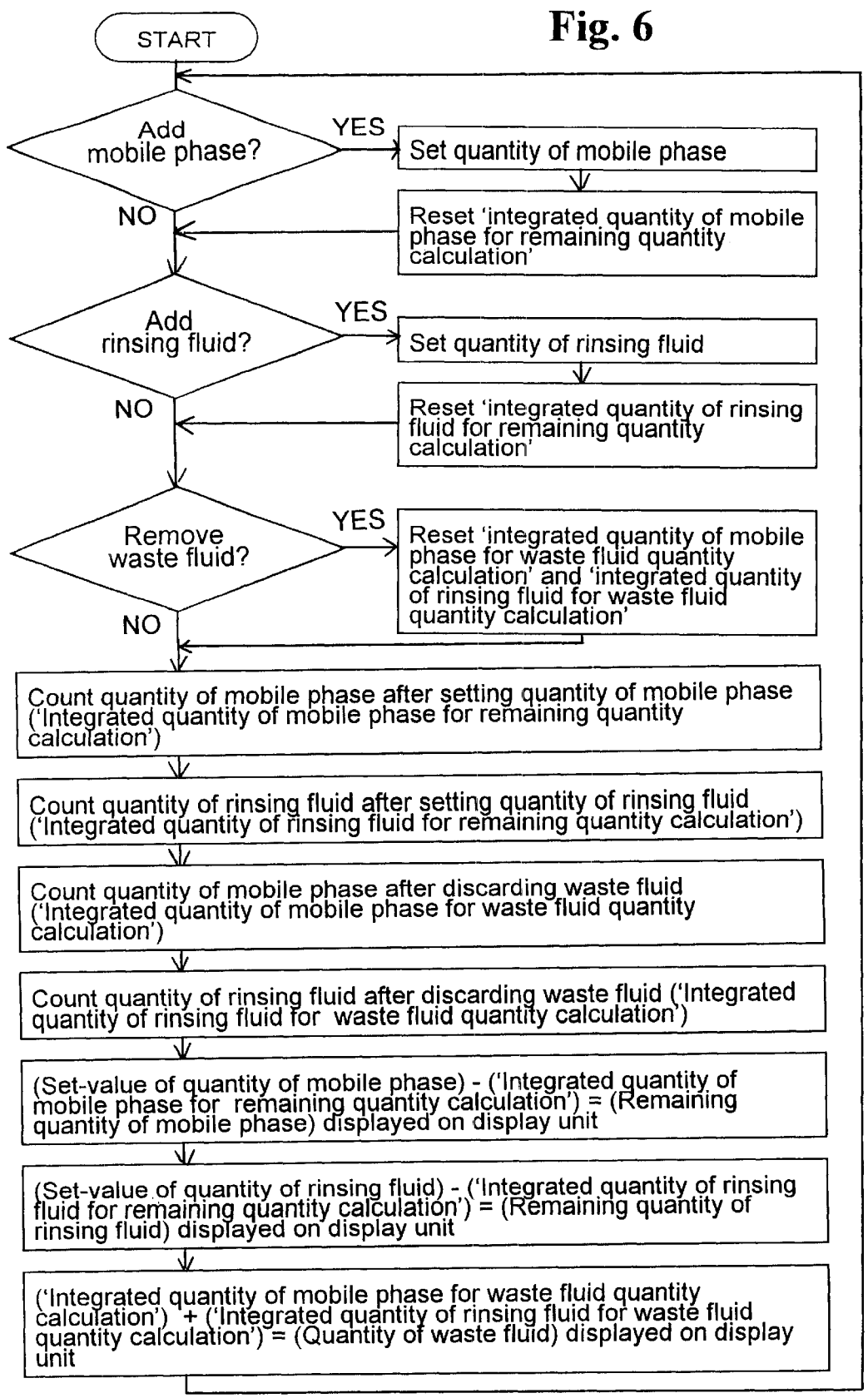
FIG. 6 is a flowchart of an operation to calculate a remaining quantity of a mobile phase, a remaining quantity of a rinsing fluid, and a quantity of a waste fluid in the same example shown in FIG. 4.

FIG. 6 is a flowchart for the operation of calculating the remaining quantity of the mobile phase, the remaining quantity of the rinsing fluid, and the quantity of the waste fluid in this example. The operation will be explained below by using FIG. 3 to FIG. 6.

Whether or not the mobile phase has been added to the mobile phase reservoir 22 is judged by the CPU 40. The RAM 44 memorizes the value of the integrated quantity of the mobile phase sent by the fluid pump 24 after the mobile phase has been added (this shall be referred to as "integrated quantity of the mobile phase for remaining quantity calculation"). When the mobile phase has been added, the quantity of the mobile phase stored in the mobile phase reservoir 22 at that time is set in the RAM 44, and the integrated quantity of mobile phase for remaining quantity calculation is reset.

Whether or not the rinsing fluid has been added to the rinsing fluid reservoir 30 is judged by the CPU 40. The RAM 44 also memorizes the value of the integrated quantity of the rinsing fluid used in the auto-sampling unit 28 after the rinsing fluid has been added (this shall be referred to as "integrated quantity of the rinsing fluid for remaining quantity calculation"). When the rinsing fluid has been added, the quantity of the rinsing fluid stored in the rinsing fluid reservoir 30 at that time is set in the RAM 44, and the integrated quantity of the rinsing fluid for remaining quantity calculation is reset.

Whether or not the waste fluid stored in the drainage reservoir 32 has been discarded is judged by the CPU 40. The RAM 44 memorizes the value of the integrated quantity of the mobile phase sent by the fluid pump 24 after the waste fluid has been discarded (this shall be referred to as "integrated quantity of the mobile phase for waste fluid quantity calculation") and also the value of the integrated quantity of the rinsing fluid used in the auto-sampling unit 28 after the waste fluid has been discarded (this shall be referred to as "integrated quantity of the rinsing fluid for waste fluid quantity calculation"). When the waste fluid has been discarded, the integrated quantity of the mobile phase for waste fluid quantity calculation and the integrated quantity of the rinsing fluid for waste fluid quantity calculation are reset.

After the analysis is started, the integrated quantity of the mobile phase for remaining quantity calculation, the integrated quantity of the rinsing fluid for remaining quantity calculation, the integrated quantity of the mobile phase for waste fluid quantity calculation, and the integrated quantity of the rinsing fluid for waste fluid quantity calculation are counted. Then, the remaining quantity of the mobile phase in the mobile phase reservoir 22 is calculated by subtracting the integrated quantity of the mobile phase for remaining quantity calculation from the quantity of the mobile phase set at the time when the mobile phase was added. The remaining quantity of the rinsing fluid in the rinsing fluid reservoir 30 is calculated by subtracting the integrated quantity of the rinsing fluid for remaining quantity calculation from the quantity of the rinsing fluid set at the time when the rinsing fluid was added. The waste fluid stored in the drainage reservoir 32 is calculated by adding the integrated quantity of the mobile phase for waste fluid quantity calculation and the integrated quantity of the rinsing fluid for waste fluid quantity calculation. The remaining quantity of the mobile phase, the remaining quantity of the rinsing fluid, and the quantity of the waste fluid are displayed on the display unit 8 separately.

Figure 7:
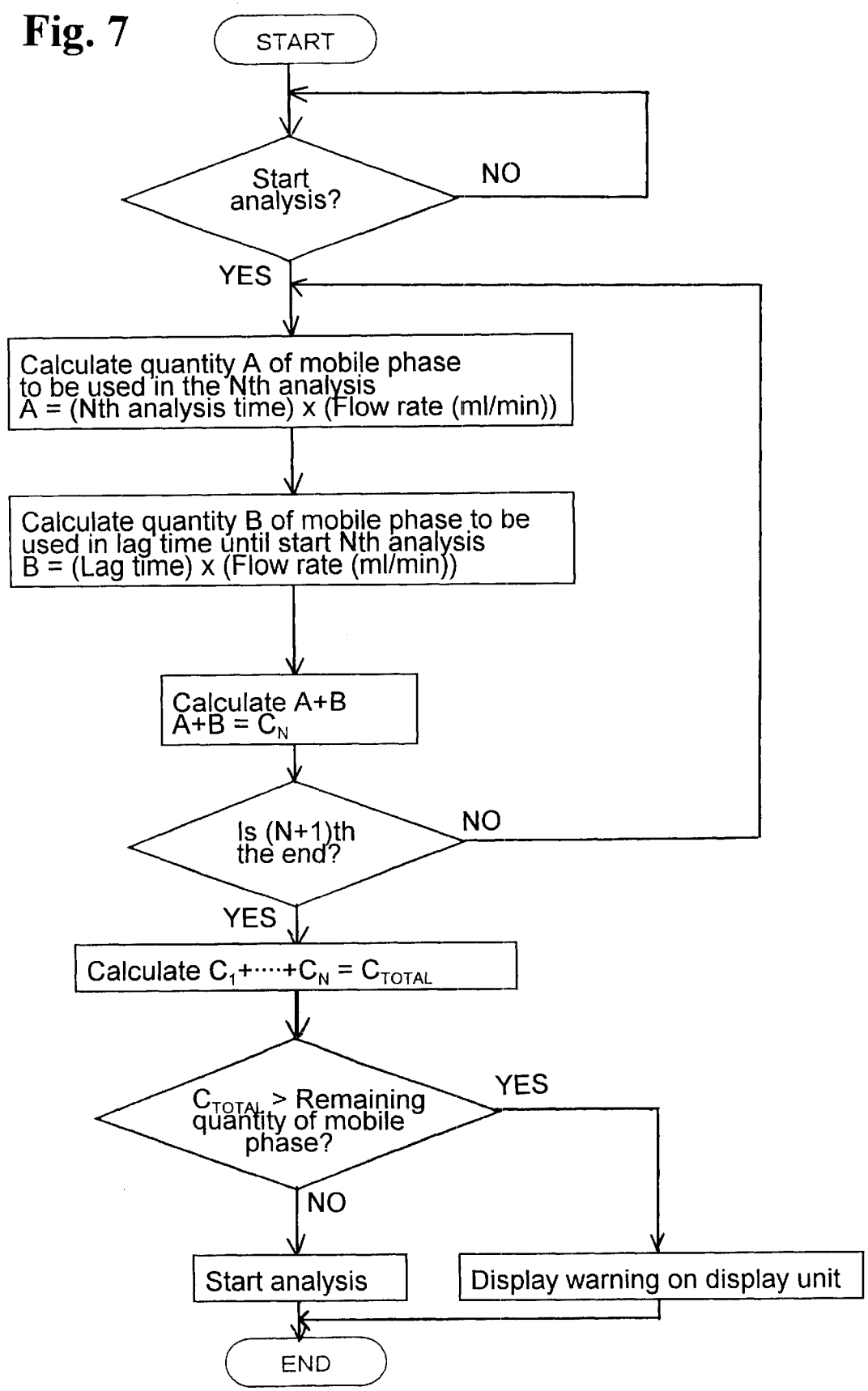
FIG. 7 is a flowchart of an operation to decide whether or not the remaining quantity of the mobile phase is sufficient for continuous analysis in the same example shown in FIG. 4.

FIG. 7 is a flowchart for the operation of deciding whether or not the remaining quantity of the mobile phase is sufficient for the continuous analysis. The operation will be explained below by using FIG. 3, FIG. 4, FIG. 5, and FIG. 7.

Once the signal to start the analysis is input, the quantity of the mobile phase required for the analysis is calculated by the CPU 40 following the analytical program stored in the RAM 44.

Quantity A of the mobile phase to be used in the Nth analysis is calculated as follows:

$$A = (Nth \text{ analysis time}) \times (\text{Flow rate of fluid pump 24 (ml/min)})$$

Quantity B of the mobile phase to be used during the lag time until the start of the Nth analysis is calculated as follows:

$$B = (\text{Lag time}) \times (\text{Flow rate of fluid pump 24 (ml/min)})$$

And quantity $C_N$ of the mobile phase required for the period from the end of the (N−1) the analysis to the end of the Nth analysis is calculated by adding the mobile phase quantities A and B.

The quantities of mobile phase $C_1, \ldots,$ and $C_N$ are calculated in order for the first analysis, ..., and the Nth analysis in the analytic program, respectively. Then, the quantity $C_{TOTAL}$ of the mobile phase required for total analysis is calculated as follows:

$$C_{TOTAL} = C_1 + \ldots + C_N.$$

The mobile phase quantity $C_{TOTAL}$ is compared with the remaining quantity of the mobile phase in the mobile phase reservoir 22 calculated following the flowchart in FIG. 6. If the mobile phase quantity $C_{TOTAL}$ is smaller than the remaining quantity of the mobile phase, the analysis is started. If mobile phase quantity $C_{TOTAL}$ is larger than the remaining quantity of the mobile phase, a warning is displayed on the display unit 8 and the analysis is not started.

In this operation, other measuring methods, such as direct measurement of the remaining quantity of the mobile phase in the mobile phase reservoir 22, may be used for determining the remaining quantity of the mobile phase into the mobile phase reservoir 22.

In the liquid chromatography of this invention, after the waste fluid stored in the drainage reservoir has been discarded and the drainage reservoir has been emptied, the waste fluid stored in the drainage reservoir is calculated based on the quantity of the mobile phase and the quantity of the rinsing fluid which are the integrated quantities of the mobile phase sent by the fluid pump and the rinsing fluid used in the sample injector, respectively, and is displayed on the display unit. Therefore, it is easy for the operator to check the quantity of the waste fluid and decide whether or not the waste fluid is discarded.

Furthermore, displaying the remaining quantities of the mobile phase and the rinsing fluid in addition to the quantity of the waste fluid enables the operator to easily check the remaining quantities of the mobile phase and the rinsing fluid.

Moreover, the quantity of the mobile phase required for the continuous analysis is calculated based on the flow rate of the fluid pump and the analytical program for the continuous analysis stored in the memory unit before the continuous analysis is started. The required quantity of the mobile phase is compared with the remaining quantity of the mobile phase and whether or not the mobile phase is sufficient for the continuous analysis is decided. If the mobile phase is sufficient for the continuous analysis, the analysis is started. If the mobile phase is insufficient for the continuous analysis, a warning is displayed. Therefore, it is not necessary for the operator to calculate the quantity of the mobile phase required for the continuous analysis and to decide whether or not the remaining quantity of the mobile phase is sufficient for the continuous analysis.

As described above, the present invention can reduce the operator's work as regards the mobile phase, the rinsing fluid, and the waste fluid.

While the invention has been explained with reference to the specific embodiments of the invention, the explanation is illustrative and the invention is limited only by the appended claims.

What is claimed is:

1. A liquid chromatography comprising:
   a column for separating a sample,
   a mobile phase reservoir connected to the column for storing a mobile phase,
   a fluid pump connected to the mobile phase reservoir for sending the mobile phase to the column,
   a sample introducing section situated between the fluid pump and the column for providing the sample into the mobile phase,
   a rinsing fluid reservoir connected to the sample introducing section and storing a rinsing fluid for cleaning the sample introducing section by the rinsing fluid,
   a drainage reservoir connected to the column and the sample introducing section for storing a used mobile phase and used rinsing fluid as waste fluid,
   a mobile phase quantity integrator associated with the fluid pump for calculating a quantity of the mobile phase sent by the fluid pump after the waste fluid in the drainage reservoir has been discarded and the drainage reservoir has been emptied,
   a rinsing fluid quantity integrator associated with the sample introducing section for integrating a quantity of the rinsing fluid used in the sample introducing section after the waste fluid in the drainage reservoir has been discarded and the drainage reservoir has been emptied,
   a waste fluid quantity calculation unit electrically connected to the mobile phase quantity integrator and the rinsing fluid quantity integrator for calculating a quantity of the waste fluid stored in the drainage reservoir based on the quantity of the mobile phase calculated by the mobile phase quantity integrator and the quantity of the rinsing fluid calculated by the rinsing fluid quantity integrator, and
   a display unit electrically connected to the waste fluid calculation unit for displaying the quantity of the waste fluid calculated by the waste fluid quantity calculation unit.

2. A liquid chromatography according to claim 1, further comprising a column oven disposed over the column for keeping the column at a constant temperature, and a detector connected to the column for detecting an isolated component separated by the column.

3. A liquid chromatography according to claim 1, wherein said mobile phase quantity integrator calculates a quantity of the mobile phase sent by the fluid pump after the mobile phase has been added to the mobile phase reservoir, and said rinsing fluid quantity integrator calculates a quantity of the rinsing fluid used in the sample introducing section after the rinsing fluid has been added to the rinsing fluid reservoir.

4. A liquid chromatography according to claim 3, further comprising:
   a mobile phase remaining quantity calculation unit electrically connected to the mobile phase quantity integrator for calculating a remaining quantity of the mobile phase stored in the mobile phase reservoir based on the quantity of the mobile phase sent by the fluid pump and integrated by the mobile phase quantity integrator after the mobile phase has been added to the mobile phase reservoir, and the stored quantity of the mobile phase in the mobile phase reservoir after the mobile phase has been added thereto,
   a rinsing fluid remaining quantity calculation unit electrically connected to the rinsing fluid quantity integrator for calculating a remaining quantity of the rinsing fluid based on the quantity of the rinsing fluid used in the sample introducing section calculated by the rinsing fluid quantity integrator after the rinsing fluid has been added to the rinsing fluid reservoir, and the stored quantity of the rinsing fluid in the rinsing fluid reservoir after the rinsing fluid has been added thereto,
   memory unit for storing an analytical program,
   a mobile phase required quantity calculation unit for calculating a quantity of the mobile phase required for a continuous analysis based on a flow rate of the fluid pump and the analytical program in the memory unit, and
   a mobile phase remaining quantity decision unit electrically connected to the mobile phase remaining quantity calculation unit and the mobile phase required quantity calculation unit for deciding whether the mobile phase is sufficient for the continuous analysis based on the remaining quantity of the mobile phase calculated by the mobile phase remaining quantity calculation unit and the required quantity of the mobile phase calculated by the mobile phase required quantity calculation unit, said mobile phase remaining quantity decision unit allowing the continuous analysis to start if the remaining quantity is sufficient and providing a warning if the remaining quantity is insufficient.

5. A liquid chromatography according to claim 4, wherein said display unit displays the remaining quantity of the mobile phase calculated by the mobile phase remaining quantity calculation unit, the remaining quantity of the rinsing fluid calculated by the rinsing fluid remaining quantity calculation unit, and decision information provided by the mobile phase remaining quantity decision unit.

6. A liquid chromatography comprising:

a column for separating a sample, a mobile phase reservoir connected to the column for storing a mobile phase, a fluid pump connected to the mobile phase reservoir for sending the mobile phase to the column, a sample introducing section situated between the fluid pump and the column for introducing the sample into the mobile phase, a column oven situated over the column for keeping the column at a constant temperature, a detector connected to the column for detecting an isolated component separated by the column, a memory unit for storing an analytical program, a mobile phase remaining quantity calculation unit for obtaining a remaining quantity of the mobile phase stored in the mobile phase reservoir, a mobile phase required quantity calculation unit electrically connected to the memory unit for calculating a quantity of the mobile phase required for a continuous analysis based on a flow rate of the fluid pump and the analytical program in the memory unit, a mobile phase remaining quantity decision unit electrically connected to the mobile phase remaining quantity calculation unit and the mobile phase required quantity calculation unit for deciding whether the mobile phase is sufficient for the continuous analysis based on the remaining quantity of the mobile phase calculated by the mobile phase remaining quantity calculation system and the required quantity of the mobile phase calculated by the mobile phase required quantity calculation unit, said mobile phase remaining quantity decision unit allowing the continuous analysis to start if the mobile phase is sufficient and providing a warning if the mobile phase is insufficient, and a display unit electrically connected to the mobile phase remaining quantity decision unit for displaying the warning given by the mobile phase remaining quantity decision unit.

* * * * *